United States Patent [19]

Rossing et al.

[11] 4,324,252

[45] Apr. 13, 1982

[54] MEMORY CONTROL CIRCUITRY FOR IMPLANTABLE MEDICAL DEVICES

[75] Inventors: Martin A. Rossing, Ramsey; Ray S. McDonald, St. Paul, both of Minn.

[73] Assignee: Medtronic, Inc., Minneapolis, Minn.

[21] Appl. No.: 175,158

[22] Filed: Aug. 4, 1980

[51] Int. Cl.³ .............................................. A61N 1/36
[52] U.S. Cl. .............................................. 128/419 PG
[58] Field of Search ................. 128/419 PG, 419 PS; 365/228

[56] References Cited

U.S. PATENT DOCUMENTS 4,103,348 7/1978 Fagan .............................. 365/228
4,197,850 4/1980 Schulman ..................... 128/419 PG

FOREIGN PATENT DOCUMENTS 542246 2/1977 U.S.S.R. .............................. 365/228
568973 8/1977 U.S.S.R. .............................. 365/228

OTHER PUBLICATIONS

DeMong, "IBM Technical Disclosure Bulletin", vol. 18, No. 12, May, 1976, pp. 4147-4149.

Primary Examiner—William E. Kamm
Attorney, Agent, or Firm—Robert C. Beck; John L. Rooney; Joseph F. Breimayer

[57] ABSTRACT

Memory control circuitry for use in a pacemaker or other medical device for setting volatile memory to a known configuration if the battery voltage and/or current drops below the level required for reliable operation of the memory devices.

4 Claims, 2 Drawing Figures

MEMORY CONTROL CIRCUITRY FOR IMPLANTABLE MEDICAL DEVICES

BACKGROUND OF THE INVENTION

1. Field of the Invention

This invention relates to pacemakers or other implantable medical devices which utilize volatile memory for the storage of information, and more particularly, to circuitry for both controlling access to the memory and for altering the state of memory under conditions of reduced power.

2. Description of the Prior Art

Cardiac pacemakers for supplying electrical stimulation of the heart in the absence of natural heartbeats are well-known in the art. Traditionally, these pacemakers have been manufactured utilizing discrete analog circuitry. However, more recently designed pacemakers utilize monolithic digital circuitry of great complexity. This additional capability has been exploited to implement desirable features such as programmability which enables the attending physician to non-invasively alter the operating parameters of the pacemaker. Typically, these programmable pacemakers use erasable or volatile memory to store the programmed information. See, for example, U.S. patent application Ser. No. 91,279 filed Nov. 5, 1979 to McDonald et al which discloses a pacemaker having a 23-bit memory for storing a digital word, used to control pulse width and pacing rate, among other variables. This digital word enters the pacemaker through a telemetry system which WRITES the digital word into volatile memory. In operation, logic within the pacemaker periodically READS the value of the word and uses this information to govern the operation of the pacemaker. The contents of the memory are accessed through an address decoder network which identifies the memory cells which will be read from or written to. During the WRITE operation the selected memory cell is addressed through the address decoder network and the appropriate logic level of the data to be stored is supplied to the WRITE input of the memory cell. After the data is presented to the memory cell a control signal is developed and applied to an ACCEPT input which permits the data to be transferred from the WRITE input into the memory flip-flop. In this context the term flip-flop includes any structure which provides a bistable structure for storing data. Consequently, it is important to preserve the integrity of this information during all operating conditions of the device.

The problem of maintaining the integrity of data stored in volatile memory is made difficult both by the nature of the power supply powering the pacemaker and by the existence of electromagnetic interference from cautery or defibillation within the pacemaker's operating environment.

Programmable pacemakers are typically powered by a primary battery which depletes during the operating life of the pacemaker. This depletion process is accompanied by a general increase in the internal battery impedance and a decline in the output voltage of the battery. These power supply characterisitics may result in a reduction in the power available to the memory circuitry of the pace-maker during certain operating conditions. If a WRITE operation is initiated when the power level is below a predetermined minimum safe operating level, an erroneous data transfer may occur and the previously stored information will be lost. Likewise, if the reduced power condition extends for a long period of time, the information contents of the memory cells may be lost due to leakage currents in the memory cells and the integrity of the data may be compromised.

Consequently, it is desirable to protect the integrity of information stored in memory by preventing WRITE operations from occuring during periods of low power. Also, it is desirable to force the contents of memory to some known configuration if the low power condition exceeds some predetermined time interval.

SUMMARY OF THE INVENTION

The memory control system of the present invention responds to a reduction in the power supplied to the memory cells and presets the memory cells to a known configuration when the power supply returns to normal. In an alternate embodiment, the memory control system permits the operating voltage to drop below a predetermined minimum level for a short period of time without resetting the volatile memory to the known configuration.

Within the control of the invention the known memory configuration would result in the operation of the pacemaker at nominal pacing parameters which are unlikely to be injurious to the pacemaker patient. This ensures that the loss of integrity of information stored in the volatile memory will result in the fail-safe operation of the pacemaker.

The structure of the present invention includes volatile memory cells having WRITE, READ, CONTROL and PRESET inputs. The PRESET input is provided for presetting the memory cells to the known data configuration which corresponds to a safe operating condition for the medical device. The structure of the intion also includes a power monitor which is responsive to the power delivered to memory cells. The monitor initiates the preset operation when the power supply fails to meet preset criteria.

DESCRIPTION OF THE PREFERRED EMBODIMENT

Figure 1:
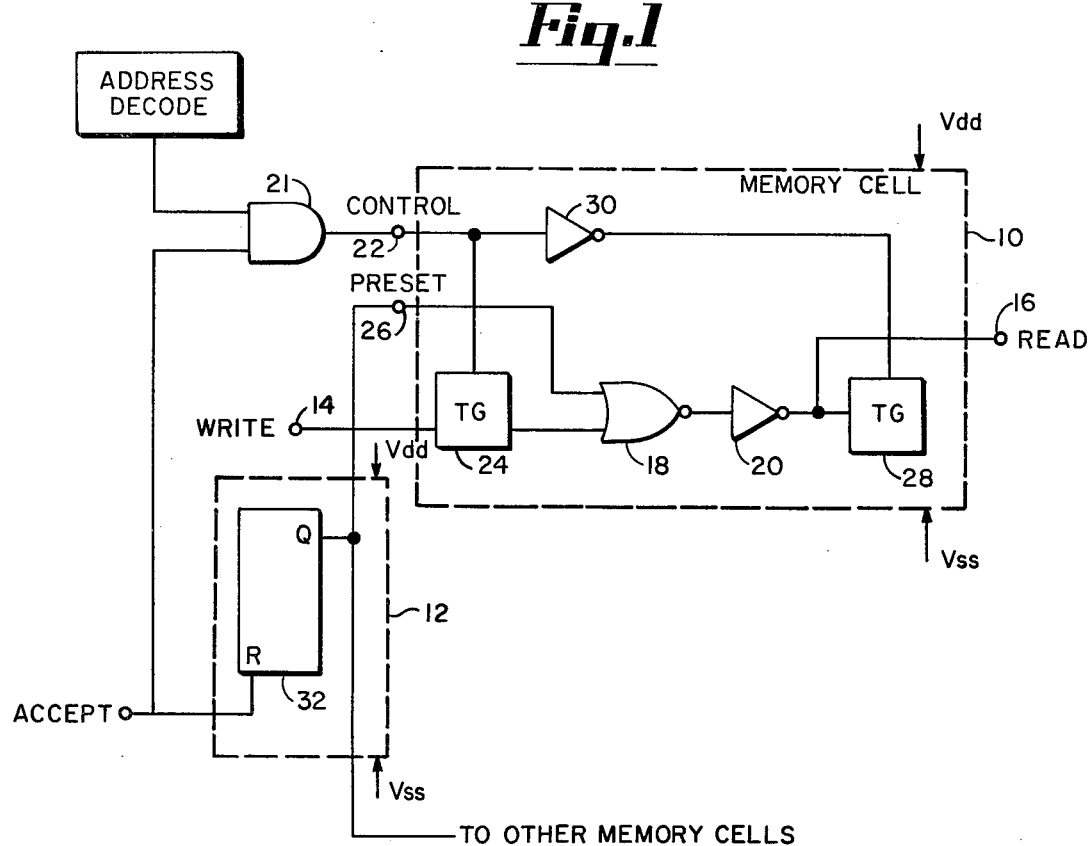
FIG. 1 is a schematic diagram illustrating the first embodiment of the present invention; and, FIG. 2 is a schematic diagram illustrating an alternate embodiment of the invention.

As shown in FIG. 1 the major functional elements of the invention include at least one memory cell 10 and a power monitor circuit 12. Both the power monitor and the memory cell are connected to the power supply through suitable connections Vdd and Vss. It is conventional in implanted medical devices to utilize CMOS circuitry to minimize power dissipation by the device. The power supply for connections to CMOS circuitry are designated Vdd for the train voltage supplied by the positive terminal of the battery and Vss for the source voltage supplied by the negative or ground terminal of the battery. Appropriate Vdd and Vss designations are shown in the figure to indicate that the memory cells and battery monitoring circuit are supplied with these system voltage levels.

During normal operation information in the form of a logic voltage level at WRITE input 14 is stored within memory cell 10 and available to READ input 16. The transfer of information from the WRITE input to the storage latch formed by NOR gate 18 and NOT gate 20 is controlled by the state of control AND gate 21. A logic one level at CONTROL input 22 closes transmission gate 24 permitting the logic level at the WRITE input 14 to be transferred to NOR gate 18. NOR gate 18 has the truth table of an inverter when the preset input is low and as a consequence, the logic level available to READ input 16 will be identical to that at WRITE input 14. When the control line 22 goes low, the transmission gate 24 is closed and transmission gate 28 is opened permitting the voltage level to be latched by the NOR gate 18 and inverter 20.

If, however, the PRESET input 26 is at the logic one voltage level, the output of NOR gate 18 will be a logic zero regardless of the other input of the NOR gate 18. In this condition the preset input forces the READ input to a logic one voltage level regardless of the value of data available at WRITE input 14 or the previous state of the READ input.

In practice, the Q output of the power monitor flip flop 32 will be connected to a number of other memory cells forcing them to the logic one condition when the Q output of the power is in the logic one state. This collelction of known memory cells will be set or reset and the information thus stored will correspond to a safe operating configuration for the medical device. However, during normal operation the power monitor 12 will place a logic zero voltage level on the appropriate PRESET inputs of the memory cells and will not interfere with their normal operation.

The monitor circuit 12 of FIG. 1 comprises a high leakage flip-flop 32 which prefers to be in the reset condition with a logic zero voltage level at the Q output. This characteristic of the flip-flop is determined during the fabrication of the integrated circuit as is well known in the art. Process or geometry changes to this flip-flop causes its leakage current to be higher than other flip-flops which form the memory cells of the device. As a consequence, in the quiescent state the leakage current of flip-flop 32 will force the flip-flop to the set condition prior to the loss of data integrity by the remaining flipflop in the memory cell. Thus, during operation a momentary reduction in operating voltage Vdd will be ignored by the power monitor circuitry 12 unless this voltage drop supplies sufficient power to flip-flop 32 to overcome its leakage current. In the event that the power supply fails to meet this power requirement the power monitor flip-flop 32 will toggle to the SET condition which will place a logic one voltage level on the PRESET inputs of the memory cells forcing them to known configuration as previously described.

Figure 2:
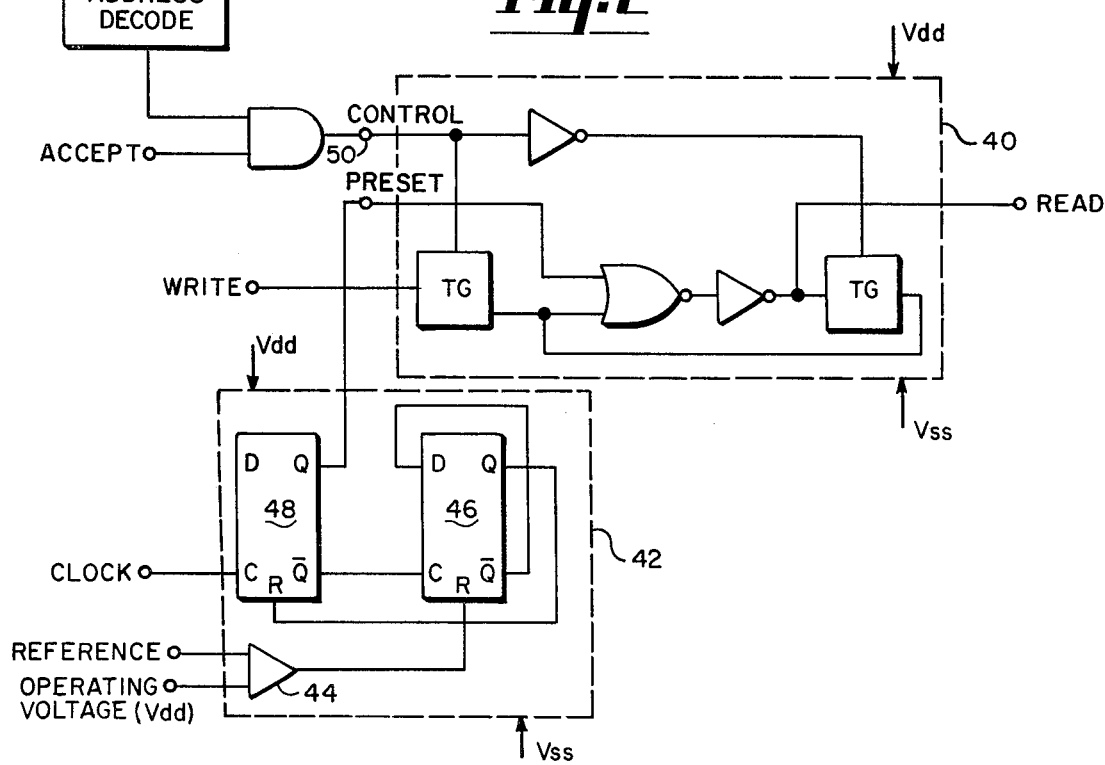

Turning to FIG. 2, there is shown a second or alternate embodiment of the present invention. Memory cell 40 operates in an analagous fashion to memory cell 10 previously discussed. The memory cells 10 and 40 as shown in the diagram include transmission gates 24 and 28 as well as NOR gate 18 to form a bistable storage means which is termed generically a flip-flop. Although the internal structure of the memory cell is disclosed to facilitate an understanding of the operation of the battery monitoring circuitry it should be clear that other memory cell structures which are known in the art may be substituted for the specific flip-flop structure shown as 10 and 40. The power monitor circuit 42, however, differs from the mode of operation of power monitor circuit 12 of FIG. 1. The power monitor 42 includes a comparator and is responsive to the difference between the operating voltage and reference voltage. The reference voltage represents a voltage greater than the sum of the worst case P- and N-channel voltage drops of the memory cells.

The comparison operation occurs in comparator 44 which has a logic zero output state when the operating voltage exceeds the reference voltage. The comparator output is connected to the reset input of D-type flip-flop 46 which is normally in the set condition with a logic one voltage level at its Q output. This logic one voltage level is applied to the reset input of flip-flop 48 which resets the Q output of flip-flop 48 to the logic zero level permitting memory WRITE operations to be controlled by control input 50 in a manner analagous to that discussed with reference to FIG. 1.

If the reference voltage exceeds the operating voltage, then the comparator output state goes high which resets flip-flop 46 to a logic zero condition at its Q output. This signal is communicated to the reset input of flip-flop 48. This permits the next logic transition at clock input C of flip-flop 48 to toggle the Q output of flip-flop 48 to the logic one condition thus forcing memory cell 40 to a known configuration. Subsequent clock pulses have no effect on the logic level at the PRESET input, until the operating voltage exceeds the reference voltage. Then the reset of flip flop 46 goes low permitting the Q output of flip flop 46 to toggle to a logic "1". Also, the NOTQ output of flip flop 48 toggles to a logic "1", thus permitting the Q output of flip flop 46 to keep flip flop 48 reset and thereby holding off a RESET to the memory cells.

Having thus described the invention it is clear that other modifications and embodiments are possible. Therefore it should be understood that within the scope of the appended claims, the invention may be practised otherwise than as specifically described.

What is claimed is:

1. Memory control system for use in an implantable medical device of the type having volatile memory cells for the storage of information comprising:

a plurality of volatile memory cells, each having a memory WRITE input, a memory READ input, a CONTROL input and a PRESET input wherein a signal coupled to said PRESET input is used for presetting said memory cells to a known configuration corresponding to a safe operating condition for the device; and power monitor means for monitoring the power available to said memory cells and for producing a power monitor output signal coupled to said PRESET input when the power available to said memory cells fails to meet specific criteria.

2. The memory control system of claim 1 wherein said power monitor means comprises:

a voltage comparison means for comparing system operating voltage to a reference voltage; and logic means responsive to said voltage comparator means for generating said PRESET signal.

3. The memory control circuitry of claim 1 wherein said power monitor means comprises a D-type flip-flop exhibiting current leakage at a current leakage rate greater than the leakage rate of said memory cells, and producing a power monitor output transition when said leakage exceeds a predetermined amount.

4. The memory control system of claim 2 wherein said logic means includes a first D-type flip-flop providing a PRESET signal from its Q output which is normally reset to zero by the Q output of a second D-type flip-flop which is normally reset to zero by the output of said voltage comparison means.

* * * * *